United States Patent [19]

Gray et al.

[11] Patent Number: 4,859,600

[45] Date of Patent: Aug. 22, 1989

[54] RECOMBINANT PROCARYOTIC CELL CONTAINING CORRECTLY PROCESSED HUMAN GROWTH HORMONE

[75] Inventors: Gregory L. Gray, San Francisco; Herbert L. Heyneker, Burlingame, both of Calif.

[73] Assignee: Genentech, Inc., South San Francisco, Calif.

[21] Appl. No.: 186,493

[22] Filed: Apr. 26, 1988

Related U.S. Application Data

[62] Division of Ser. No. 488,232, Apr. 25, 1983, Pat. No. 4,755,465.

[51] Int. Cl.[4] .................. C12N 1/16; E12N 15/00; C07K 13/00
[52] U.S. Cl. ...................... 435/252.33; 435/172.3; 435/252.34; 435/252.3; 530/399
[58] Field of Search ............ 435/172.3, 70, 253; 530/399

[56] References Cited

U.S. PATENT DOCUMENTS

| | | | |
|---|---|---|---|
| 4,332,717 | 6/1982 | Kanooka et al. | 530/854 |
| 4,338,397 | 7/1982 | Gilbert et al. | 435/68 |
| 4,342,832 | 8/1982 | Goeddel et al. | 435/172 |
| 4,621,053 | 11/1986 | Sugimoto | 530/399 |
| 4,755,465 | 7/1988 | Gray et al. | 435/70 |

FOREIGN PATENT DOCUMENTS

| | | |
|---|---|---|
| 0020147 | 12/1980 | European Pat. Off. |
| 0020251 | 12/1980 | European Pat. Off. |
| 0047600 | 3/1982 | European Pat. Off. |
| 0055942 | 7/1982 | European Pat. Off. |
| 0088632 | 9/1983 | European Pat. Off. |
| 01114695 | 8/1984 | European Pat. Off. |
| 2091268 | 7/1982 | United Kingdom |
| 2121054 | 12/1983 | United Kingdom |

OTHER PUBLICATIONS

Robins et al., From Gene to Protein: Translation Into Biotechnology, pp. 275–288, Academic Press Inc. (1982).
Mills et al., Endocrinology, vol. 107, pp. 391–399 (1980).
Reagan et al., Endocrinology, vol. 109, pp. 1663–1671 (1981).
Seeburg et al., DNA 2(1):37–45 (1983).
Sussman, P. M. et al., P.N.A.S. U.S.A. 73(1):29–33 (Jan. 1976).
Jackson, R. C. et al., P.N.A.S. U.S.A. 74(12):5598–5602 (Dec. 1977).
Goeddel et al., Nature 281:544–548 (1979).
Guarente et al., Science 209:1428–1430 (1980).
Keshet et al., Nuc. Acids Res. 9(1):19–30 (1981).
Davis et al., Nature 283:433–438 (1980).
Talmadge et al., PNAS U.S.A. 77(6):3369–3373 (1980).
Talmadge et al., PNAS U.S.A. 77(7):3988–3992 (1980).
Zemel-Dreasen et al., Gene 27:315–322 (1984).
Kadonaga et al., J. Biol. Chem. 259(4):2149–2154 (1984).
Ohsuye et al., Nucl. Acids Res. 11(5):1283–1294 (1983).
Silhavy et al., Micro. Bio. Rev. 47(3):313–344 (1983).
Wood et al., J. Bact. 145(3):1448–1451 (1981).
Taniguchi et al., PNAS U.S.A. 77(9):5230–5233 (1980).
Martial et al., Science 205:602–607 (1979).
DeBoer et al., Promoters, Structure & Function; Rodriguez et al., Ed. Praeger Scientific, pp. 462–481 (1982).
Sakaguchi et al., Current Topics in Microbiology and Immunology 96:31–45 (1982).

Primary Examiner—Alvin E. Tanenholtz
Attorney, Agent, or Firm—Max D. Hensley

[57] ABSTRACT

The production of mature hGH in E coli and Pseudomonas strains transformed by a plasmid which encodes pre hGH (comprising the signal polypeptide and the hormone itself) is described. These prokaryotes process the pre-hGH to cleave the signal sequence and, thereby, produce mature hGH.

1 Claim, 1 Drawing Sheet

RECOMBINANT PROCARYOTIC CELL CONTAINING CORRECTLY PROCESSED HUMAN GROWTH HORMONE

This application is a division, of application Ser. No. 488,232, filed Apr. 25, 1983.

FIELD OF INVENTION

This invention relates to the production of human growth hormone (hGH) with is signal peptide (pre-human growth hormone) in E. coli and Pseudomonas and processing of the unprocessed (pre) protein by the bacterial host to cleave the signal sequence from the hGH portion of the protein to produce mature hGH.

BACKGROUND

Human growth hormone (hGH) is secreted in the human pituitary. In its mature form it consists of 191 amino acids, has a molecular weight of about 21,500, and thus is more than three times as large as insulin. Until the advent of recombinant DNA technology, hGH could be obtained only by laborious extraction from a limited source—the pituitary glands of human cadavers. The consequent scarcity of the substance has limited its application to treatment of hypopituitary dwarfism even though it has been proposed to be effective in the treatment of burns, wound healing, dystrophy, bone knitting, diffuse gastric bleeding and pseudarthrosis. In fact, available estimates are that the amount of hGH available from tissue is adequate only to serve about 50 percent of the victims of hypopituitary dwarfism. Thus, no hGH is available for other applications.

Recently, it has been shown that hGH can be produced in a recombinant host cell, specifically E. coli in quantities which would be adequate to treat hypopituitary dwarfism and the other conditions for which it is effective. See, for example, U.S. Pat. No. 4,342,832. While this advance in the art promises relief to those who suffer the afflictions for which it offers hope of amelioration, for reasons which are set forth below, the hGH obtained using the process of U.S. Pat. No. 4,342,832 contains at least a substantial amount of hGH to which the amino acid methionine not found in native hGH is appended at the N-terminal end of the protein. While there is no evidence that this slightly different hGH will, in sensitive individuals, cause any important undesirable side reactions it is, nevertheless, structurally distinct from "mature" hGH. Hormones which differ slightly from those produced by the human body, such as various insulins obtained as tissue extracts of cattle and other animals, have been successfully used to treat human disease for many years. Nevertheless, the advent of recombinant DNA techniques have made it possible to obtain insulin of precisely the same amino acid sequence as that produced by the body. This has been hailed not only as a great scientific advance but a medical one as well since the availability of a process for making human insulin promises to reduce the risk of adverse side reactions attendant with ingestion of animal insulin to those who suffer diabetes. Therefore, notwithstanding the availability of hGH in an active form which differs only slightly from that occurring naturally, there remains a need to obtain hGH conveniently which, in its amino acid content, consists solely of the 191 amino acid sequence of the hGH produced by the pituitary. Further, the herein invention discloses the production of met-less hGH in commercially practicable amounts.

The use of recombinant DNA technology to obtain vectors for expressing heterologous DNA in a transformed microbial host is now a well established science. The first successes in this field were achieved using strains of the gram-negative bacterium E. coli such as E. coli K-12, strain 294.

The use of E. coli as a microbial host for obtaining complex heterologous polypeptides has its limitations however. Relatively small polypeptides must be obtained as a fusion protein in which the target polypeptide is expressed as part of a larger polypeptide in order to protect the small protein from degradation by the host cell. For most purposes, the small protein produced as a fusion protein must be cleaved in some way from the larger molecule to obtain a useful product.

Large foreign proteins are not degraded by the cell and can be produced directly if the gene for their direct expression, including the appropriately placed start codon, is linked to a suitable promoter gene, such as the well known lac promoter. The signal to begin translation of the mRNA coding sequence is the AUG generated from the ATG gene codon which also codes for the amino acid methionine (Met). Because prokaryotes sometimes do not remove the N-terminal Met from the resulting protein, expression of heterologous DNA under control of a bacterial promoter and in a bacterial host sometimes results in a protein whose first amino acid is methionine. Results to date, for example, with production of hGH in E. coli, have shown that the host cell has only a limited ability to cleave methionine intracellularly and there is no convenient way to do so extracellularly. Accordingly, as noted above, microbially expressed hGH by the process of U.S. Pat. No. 4,342,832 leads to a product in which at least a substantial portion of the hGH has the appended methionine group which, in some circumstances, may cause the protein to be recognized as a foreign protein when used in therapeutic applications.

Many naturally occurring proteins are initially expressed in their normal environment with an additional peptide sequence which permits the protein to pass through a cellular membrane of the cell in which it is manufactured. The additional peptide, which is cleaved in this process, is referred to as a "signal" peptide. If a heterologous gene which included the gene for a signal sequence were placed under control of a bacterial promoter and the bacterium would cleave the signal sequence intracellularly, the mature protein without an appended methionine moiety could be obtained. However, unless cleaved by the host, the signal sequence actually complicates isolation of the mature protein since extracellular cleavage is not easily accomplished.

Efforts to produce "immature" protein, i.e., the protein of interest coupled to a signal sequence, in E. coli have suggested that gram-negative bacteria such as E. coli do not effectively process this protein to cleave the signal sequence, however. A small protein preproinsulin, has been shown to be partly processed to remove the signal peptide in E. coli. However, no success at all has been obtained with large molecules such as fibroblast and leukocyte interferons. In the case of fibroblast interferon, no biologically active material was produced (Taniguchi, T. et al., Proc. Natl. Acad. Sci. USA 77, 5230–5233 (1980)). In the case of the leukocyte interferons, biologically active material was produced but was neither transported nor properly processed.

SUMMARY OF THE INVENTION

We have found, unexpectedly, that the gene for pre-hGH, i.e., a gene coding for the 191 amino acids of the mature protein and the 26 amino acids of its signal peptide, is expressed to give pre-hGH in gram-negative bacteria which is then processed in the cell to cleave the signal peptide from the mature protein. (Pre-hGH or pre-protein refers to the desired protein containing a signal sequence which, in its native environment effects secretion of the desired protein.) As a result, hGH is obtained in its mature form, and in an environment in which it is free of other proteins associated with its native environment. Thus, using the process of the invention it can be obtained free of proteins of human origin, in commercially useful amounts, and without the superfluous methionine in addition to the amino acid sequence of the naturally occurring protein.

The present invention also provides replicable vectors for the expression of the gene for the immature protein which can be used in both E. coli and Pseudomonas and other prokaryotic bacterial species. The invention further provides prokaryotic hosts transformed by such vectors.

An object of the present invention, therefore, is an improved process for obtaining hGH by recombinant DNA technology.

Yet another object is to obtain hGH which is free of appended amino acids not found in the natural form.

The achievement of these and other objects will be apparent from the following discussion of presently preferred embodiments.

DETAILED DESCRIPTION OF THE INVENTION

The general approach to the invention is the preparation of an expression vector or cloning vehicle which is replicable in the host prokaryote and which contains a DNA sequence which codes for expression of immature hGH operably connected to a DNA which effects expression. As used herein, "prokaryote" refers to cells which do not contain a nucleus and whose chromosomal material is thus not separated from the cytoplasm. Prokaryotes include, for example, bacteria but do not include such nucleated microorganisms as yeast.

Specifically, plasmids were constructed as expression vectors which could be used to transform both E. coli and Pseudomonas strains in order to demonstrate the ability of bacterial hosts to effect expression of pre-hGH and process it to cleave the signal sequence.

It has been shown previously that the E. coli plasmid pBR322, which is the basic plasmid modified for expression of heterologous DNA in E. coli, can be maintained stably in Pseudomonas (Ps.) aerugenosa (a.) if cloned in the broad host range, sulfonamide resistant ($Su^R$), streptomycin resistant ($Sm^R$) plasmid RSF1010, which is also an E. coli plasmid. See Wood et al., J. Bacteriol., 14, 1448 (1981) an Sakagouchi, current Topics in Microbiology and Immunology, 96, 31 (1982). Therefore, to obtain plasmids which would code for hGH and which could be used to transform both E. coli and Ps. strains, we determined to prepare hybrid plasmids of pBR322 and pRSF1010 which contained genes for the expression of that protein.

Figure 1A:
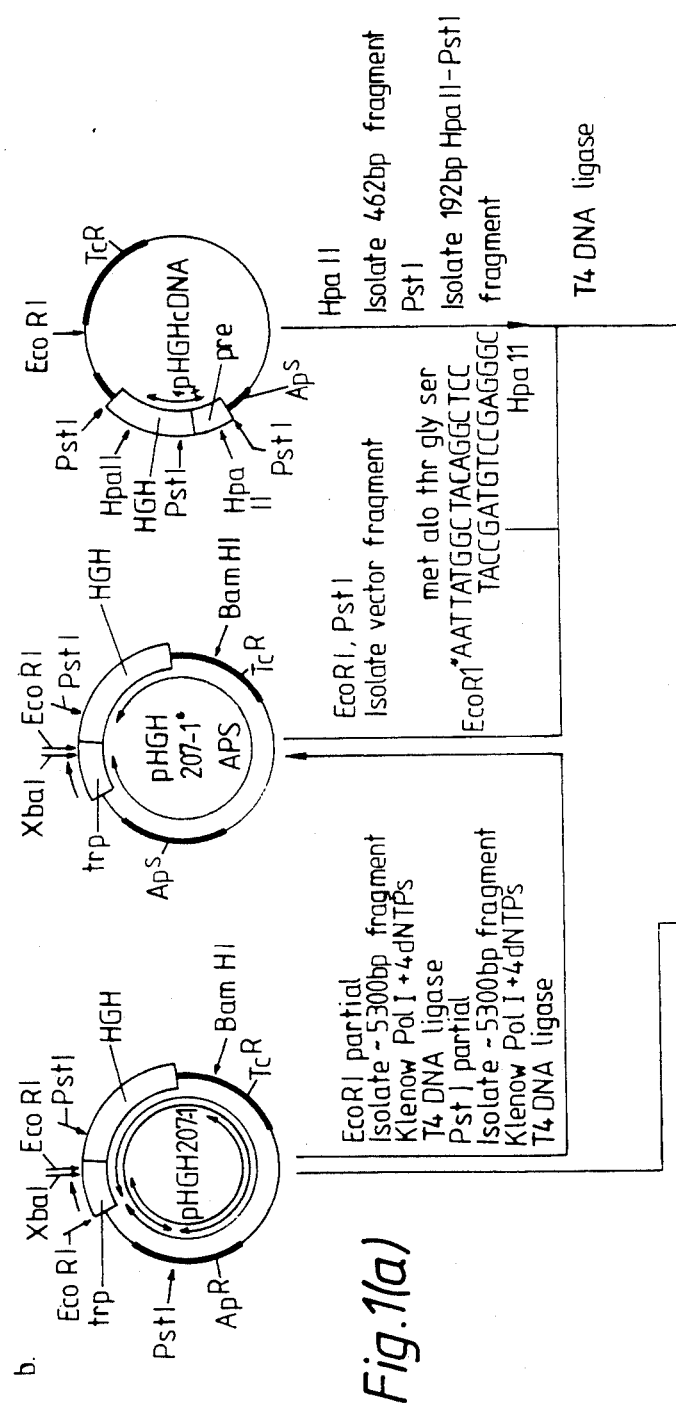
FIG. 1A depicts the amino acid sequence and mRNA sequence of the signal polypeptide associated with native hGH and FIG. 1B shows the construction of the hGH expression plasmid pRPH2.
Figure 1B:
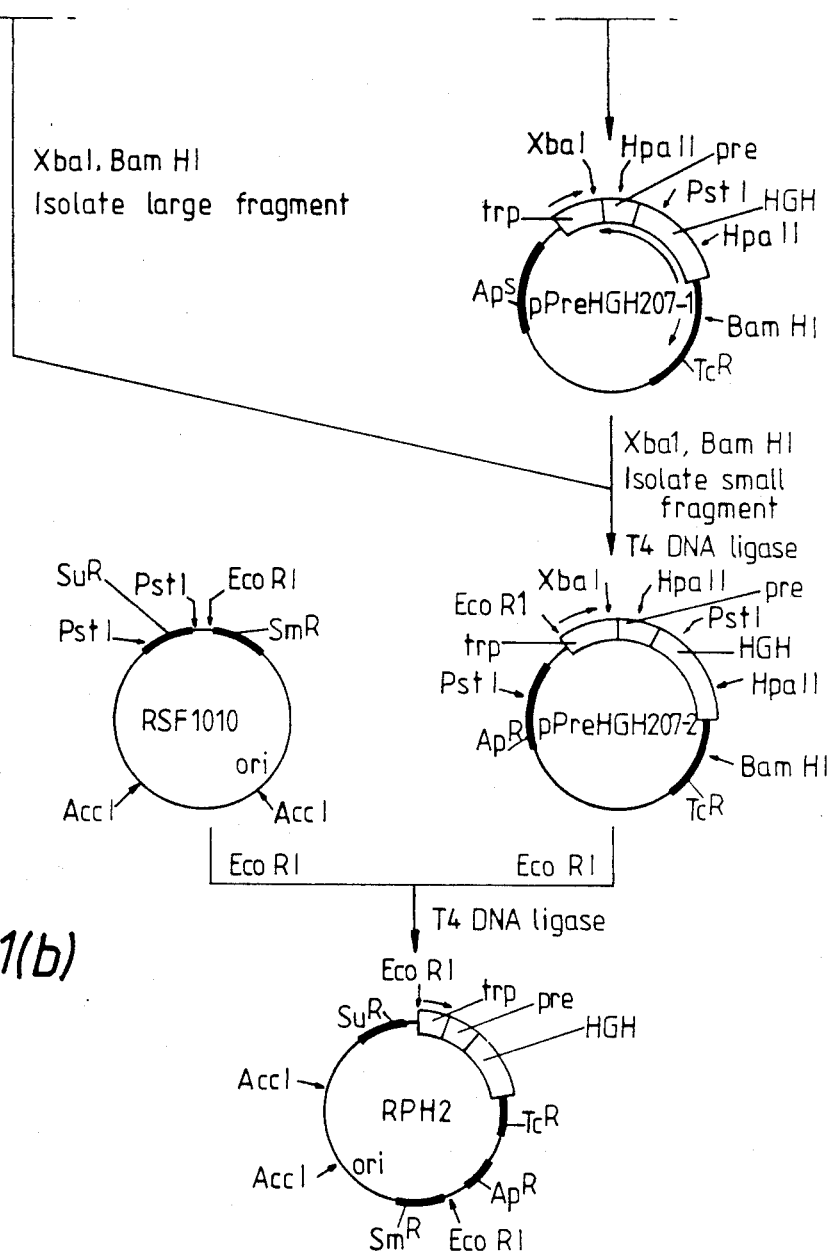

The construction of a plasmid to code for the expression of immature hGH, i.e., for the 191 amino acids of hGH linked to the 26 amino acids of its signal sequence, is shown in FIG. 1B. The construction uses a pBR322 derivative, plasmid phGH207-1 described in de Boer, H. et al. Promoters: Structure and Function, eds. Rodriguez, R. and Chamberlin, M.J. (Praeger, New York), 462–481 (1982). The phGH207-1, designated 1 in FIG. 1B, was partially digested with EcoRI and the largest fragment purified by electrophoresis on polyacrylamide gel. This fragment was subjected to second strand synthesis with DNA polymerase Klenow fragment and ligated with T4 DNA ligase to form a plasmid, phGH207-1*, with a unique EcoRI site at the junction of the trp promoter-ribosome binding site and the hGH structural gene. The phGH207-1* was partially cleaved with PstI and the largest fragment purified by electrophoresis on a polyacrylamide gel. This fragment was subjected to second strand synthesis with DNA polymerase Klenow fragment and ligated with T4 DNA ligase to form plasmid phGH207-1*-APS, designated 2 with a unique PstI site within the hGH structural gene. The phGH207-1*-APS was digested to completion with EcoRI and PstI and the largest fragment purified by gel electrophoresis using a polyacrylamide gel. This fragment contains the trp promoter and the 5' end of the gene of mature hGH.

A second plasmid, phGHcDNA designated 4 in FIG. 1B, was prepared as described by Martial et al., Science 205, 602–606 (1979) and treated with HpaII to excise a 462 base pair (bp) fragment which codes for most of the signal peptide DNA sequence of hGH and the amino terminal portion of mature hGH. This fragment was purified by gel electrophoresis using polyacrylamide gel. This fragment was digested with PstI to excise a 192 bp fragment which codes for most of the signal peptide DNA sequence of hGH and the amino-terminal portion of mature hGH. This fragment was purified by gel electrophoresis using polyacrylamide gel.

Referring now to FIG. 1A, there is shown the amino acid and mRNA sequences for the signal polypeptide of immature hGH with codons AUG for f-Met, the signal for initiation of translation in bacteria, which reveals that the HpaII site is near the 5' end. To complete the gene for the signal sequence and to provide EcoRI and HpaII sites, the two synthetic oligonucleotides 2 in FIG. 1B were synthesized by the improved triester method of Crea, Proc. Nat'l. Acad. Sci. USA, 75, 5765 (1978). Aliquots of 5 ug of each of the two synthetic oligonucleotides were phosphorylated using T4 polynucleotide kinase and [$\gamma-^{32}$P]ATP (NEN) as described by Goeddel et al, Proc. Nat'l. Acad. Sci. USA, 76, 106 (1979). The two molecules were then annealed by mixing these reaction products, heating for 5 min. at 90° C. and then cooling to 22° C.

The fragments phGH207-1 and phGHcDNA and the synthetic oligonucleotides were, in a three way ligation using T4 ligase, joined to obtain plasmid pPrehGH2-07-1, designated 5 in FIG. 1B, which was cloned in E. coli K-12, strain 294 (E. coli 294), which has been deposited with the American Type Culture Collection, ATCC Accession No. 31446, on October 28, 1976. The plasmid was isolated from a colony which was $Tc^R$. The nucleotide sequence of the region comprising the trp promoter and the codons for the hGH signal polypeptide and the amino terminal amino acids was confirmed by the dideoxy chain termination method. See Messing, J., Crea, R., and Seeburg, P.H., *Nucleic Acids Res.* 9, 309-321 (1981).

The pPrehGH207-1 and phGH207-1 were digested with XbaI and BamHI. The smaller fragment of pPrehGH207-1 was purified by gel electrophoresis and contains the entire pre hGH gene. The larger fragment of phGH-207-1 was purified by gel electrophoresis and contains the trp promoter. These two fragments were mixed and treated with T4 DNA ligase to give plasmid 6, designated pPrehGH207-2, which contains the trp promoter and the pre hGH gene. The pPrehGH207-2 and pRSF1010 designated 7 were treated with EcoRI and joined with T4 ligase to give plasmid 8, designated pRPH-2, which was used to transform *E. coli* 294. The pRPH-2 was obtained from a colony exhibiting $Tc^R$ and $Sm^R$.

The expression vector pRPH-2 was used to transform Ps.a. strain PA02003, Chandler et al, Mutat. Res., 23, 15 (1974). Cells transformed with pRPH-2 were grown overnight in Luria broth (LB) with 50 μg/ml tetracycline at 37° C. to logarithmic phase. Cell pellets were resuspended in 30 mM Tris, pH 8.0, 20Δ sodium dodecyl sulfate (SDS) and sonicated. The cell extracts were serially diluted for analysis by radioimmunoassay using a Phaedabas hGH PRIST kit (Pharmacia). Substantial levels of hGH were found ($4 \times 10^2$ ng/ml/$A_{550}$). Cell extracts were electrophoresed in 12.5 percent SDS on polyacrylamide gels. hGH was visualized by an immunoblotting technique using anti-hGH rabbit antiserum (supplied by Kabi) and $^{125}$I-labeled protein a. The cell extracts were shown by autoradiography to contain one major component reactive with anti-hGH which has the same electrophoretic mobility as authentic pituitary hGH. A minor band of somewhat lesser mobility was also detected and is presumably unprocessed pre hGH.

The major reactive component of the cell extracts was purified to homogeneity by immunoaffinity chromatography and high performance liquid chromatography, and the amino acid sequence of the amino-terminus was determined by the Edman degradation method. See Edman et al, *European J. Biochem.*, 1, 80 (1967). It was found to be homogeneous and to begin with the sequence Phe-Pro-Thr-Ala in perfect correspondence to the sequence of pituitary hGH.

Expression of pre hGH accompanied by proteolytic cleavage to obtain the mature hGH using pRPH-2 transformants of *E. coli* and Ps. putida has also been accomplished indicating that the ability of gram negative bacteria to successfully process the pre hGH, although unexpected in view of the prior failure of *E. coli* to process interferons possessing their own signal peptides, is a general phenomenon.

In view of the foregoing those skilled in the art can appreciate that modifications of the preferred embodiments can be made without departure from the spirit of the invention. For example, it is not necessary to use a plasmid of pRSF1010 if the recombinant host to be employed is *E. coli*. Thus, successful expression in *E. coli* can be achieved using, for example, pPrehGH207-1 or pPrehGH207-2 of FIGS. 1A and 1B. Accordingly, the present invention should be limited only by the lawful scope of the appended claims.

We claim:

1. A recombinant prokaryotic host cell containing human growth hormone, the amino acid sequence of which consists of the amino acid sequence of naturally occuring human growth hormone, which is free of other proteins associated with its native environment and is free of mature human growth hormone having an extraneous N-terminal methionine, and which was produced by said recombinant prokaryotic host.

* * * * *